(12) United States Patent
Carlson et al.

(10) Patent No.: US 8,770,008 B2
(45) Date of Patent: Jul. 8, 2014

(54) METHOD FOR TESTING THE FUNCTION OF A DEVICE

(75) Inventors: Mats Carlson, Täby (SE); Tryggve Hemmingsson, Sollentuna (SE)

(73) Assignee: Aerocrine AB, Solna (SE)

( * ) Notice: Subject to any disclaimer, the term of this patent is extended or adjusted under 35 U.S.C. 154(b) by 1052 days.

(21) Appl. No.: 12/808,672

(22) PCT Filed: Dec. 1, 2008
(Under 37 CFR 1.47)

(86) PCT No.: PCT/SE2008/000673
§ 371 (c)(1),
(2), (4) Date: Apr. 15, 2011

(87) PCT Pub. No.: WO2009/082318
PCT Pub. Date: Jul. 2, 2009

(65) Prior Publication Data
US 2011/0314896 A1    Dec. 29, 2011

Related U.S. Application Data

(60) Provisional application No. 61/016,356, filed on Dec. 21, 2007.

(30) Foreign Application Priority Data

Dec. 20, 2007 (SE) ..................... 0702859

(51) Int. Cl.
*G01N 33/497* (2006.01)
*G01N 1/22* (2006.01)
*G01D 18/00* (2006.01)

(52) U.S. Cl.
USPC ............... 73/1.03; 73/23.3; 422/84; 702/104

(58) Field of Classification Search
USPC ........ 2/1.03, 1.06, 23.2; 422/83, 84; 702/104, 702/116
See application file for complete search history.

(56) References Cited

U.S. PATENT DOCUMENTS

| 3,854,319 | A  | * | 12/1974 | Burroughs et al. ............ 73/1.03 |
| 7,192,782 | B2 | * | 3/2007  | Roller et al. .................. 436/116 |
| 7,992,422 | B2 | * | 8/2011  | Leddy et al. ................... 73/23.3 |
| 2004/0017570 | A1 | | 1/2004 | Parikh et al. |
| 2006/0263254 | A1 | | 11/2006 | Lee |
| 2007/0278110 | A1 | | 12/2007 | Jafari |
| 2013/0156647 | A1 | * | 6/2013 | Lueck et al. .................... 422/84 |

FOREIGN PATENT DOCUMENTS

| EP | 1211502 A2 | 6/2002 |
| WO | 2004/011924 A1 | 2/2004 |

OTHER PUBLICATIONS

International Search Report received for PCT Patent Application No. PCT/SE2008/000673, mailed on Mar. 31, 2009, 3 pages.

(Continued)

*Primary Examiner* — Lisa Caputo
*Assistant Examiner* — Punam Roy
(74) *Attorney, Agent, or Firm* — Renner, Otto, Boisselle & Sklar, LLP

(57) ABSTRACT

The function of a measuring device can be tested using a healthy person as an external control, provided that this person fulfils certain criteria and that particular method steps are adhered to.

18 Claims, 4 Drawing Sheets

(56) References Cited

OTHER PUBLICATIONS

Alving, K et al., "Performance of a New Hand-Held Device for Exhaled Nitric Oxide Measurement in Adults and Children," Respiratory Research 2006, 7:67, Biomed Central Ltd., London, GB, Apr. 20, 2006, 7 pages.

Search Report from Corresponding European Patent Application No. 08863963.8, dated Aug. 26, 2013.

* cited by examiner

METHOD FOR TESTING THE FUNCTION OF A DEVICE

CROSS REFERENCE TO RELATED APPLICATIONS

This is a U.S. National Phase patent application of PCT/SE2008/000673, filed Dec. 1, 2008, which claims priority to Swedish patent application Ser. No. SE 0702859-0 filed Dec. 20, 2007, and U.S. Provisional patent application Ser. No. 61/016,356, filed Dec. 21, 2007, all of which are hereby incorporated by reference in the present disclosure in their entirety.

TECHNICAL FIELD

The present invention relates generally to devices for measuring the concentration of a gaseous compound, and in particular to devices for measuring the concentration of a gaseous compound in exhaled breath. More specifically the present invention relates to a method of testing the function of such devices.

BACKGROUND

It is known that both inorganic and organic gaseous components in exhaled breath may provide useful insights into metabolic processes in certain diseases. The concentrations of such components have been studied in great detail in both research and clinical settings. Based on these insights, the concentration values aid in the establishing of a diagnosis, and have proven useful to monitor the well being of a patient, etc. Examples of gaseous components present in exhaled air include nitrogen monoxide, here referred to as nitric oxide (NO), carbon dioxide ($CO_2$), oxygen ($O_2$), and volatile organic compounds. One illustrative example is NO, which since it was found to be a diagnostic marker of inflammation in early 1990, has become the focus of much research. Different techniques and sensors have been suggested for use in the determination of NO concentration. Examples include, but are not limited to chemiluminescence, semiconductor-based sensors, electrochemical sensors, and polymer-based sensors.

Regardless of the identity of the gaseous component to be determined, or the technology chosen, it is important to be able to test the function, accuracy and reliability of the device.

Traditionally, reference gases are used, the reference gas being a gaseous mixture having a known and for practical purposes stable concentration of the substance to be measured by the measuring device. For example, if the measuring device is used to measure the concentration of NO in exhaled breath, a special reference gas with a known concentration of NO in nitrogen may be used. That is, the bulk gas is nitrogen which contains a specified concentration of NO. This reference gas is stored in compressed form in a gas cylinder and is then fed to the measuring device, often via a pressure regulator and a gas fitting. The reading of the measuring device is then compared with the known concentration of the substance to be measured in the special reference gas.

This technique is frequently rather expensive because of the cost of manufacturing, storing and handling the special reference gas. It is, in some cases, also technically difficult to manufacture the special reference gas within the required specifications. This is for example the case when a special reference gas with a low concentration of the substance to be measured is needed. It is also time consuming to order, transport and handle the special reference gas, which in addition may have limited shelf life. Further, the handling of the gas cylinder itself is inconvenient because of its size and weight.

Some measuring devices use pre-calibrated sensors or are otherwise pre-calibrated during manufacturing and need no calibration during their specified life-time. It would still be advantageous to have the possibility to test if the measurement value from a specific device is correct and reliable.

SUMMARY

It is an object of the present invention to provide an alternative testing method that obviates or at least reduces some or all of the drawbacks connected with the background art.

The inventors surprisingly found that the use of reference gases can be replaced, at least in part, by the use of humans as reference persons, according to an embodiment of the present invention as set forth in the attached claims, incorporated herein by reference.

The inventors make available a method of using a human control for testing the function of a device for measuring the concentration of a gaseous substance in exhaled air, the method comprising the steps of:

checking that said human control is in a normal condition,
measuring the concentration of said gaseous substance in air exhaled by said human control to obtain a current value,
determining if said current value of the measured concentration is within a specified range,
determining a reference value,
determining the difference between said reference value and said current value, and
interpreting a deviation of more than a specified value as an indication that the device is malfunctioning or in need of calibration.

According to a preferred embodiment of the invention, the specified range for the current value is adapted to the relevant diagnostic interval for the gaseous component to be determined. The expression "adapted to" here means that the specified range is chosen to be the substantially the same as the diagnostic interval, i.e. from a value normally obtained when testing a healthy individual, to a value normally obtained when testing an individual exhibiting the disease in question. Alternatively, the specified range is chosen so as to overlap the diagnostic interval. In an embodiment where the gaseous component is NO, the specified range for the current value is preferably about 10 to about 40 ppb. For other indications, where the component to be detected is another, the specified range will be another, as will be understood by persons skilled in the art.

According to a preferred embodiment, the reference value is determined by calculating a moving average based on the current value and previously obtained values from measurements with the same human control. Preferably at least two measurement values from previous measurements are used when determining the moving average, and more preferably at least three measurement values are used when determining the moving average. A skilled person will understand that beyond a reasonable amount of previous values, the relevance of the moving average calculation will not improve further.

According to a preferred embodiment, the measurements are performed at an interval of at least 2, preferably at least 3, more preferably at least 4 days but less than 8 days.

According to another embodiment, the gaseous substance is nitric oxide. A skilled person will however understand that the invention is applicable also to the determination of other gaseous components found in exhaled air, provided that they occur in a measurable and stable concentration in healthy humans. A non-exclusive list of examples includes carbon dioxide ($CO_2$), oxygen ($O_2$), and volatile organic compounds.

According to an embodiment of the invention, a human subject is considered to qualify as a control and as being in a normal condition when fulfilling the following criteria: no ongoing cold, no airway disease, no asthma, non-smoker, no allergy, no non-seasonal allergy, no intake of nitrate rich food within the last 3 hours, and no strenuous exercise performed within the last hour. Regarding the requirement of the human control not being asthmatic, it should be understood that also an asthmatic person could qualify, provided that the disease is well-controlled, e.g. by taking an anti-inflammatory drug.

Further, according to an embodiment of the invention, the interpretation of a deviation of more than a specified value as an indication that the device is malfunctioning (or in need of calibration) is preceded by, and conditional to an additional check that the control is in a normal condition.

Further possible features and benefits of the present invention will be explained in the detailed description below.

BRIEF DESCRIPTION OF THE DRAWINGS

The invention will now be described by way of non limiting embodiments and with reference to the accompanying drawings in which.

DETAILED DESCRIPTION

Figure 1A:
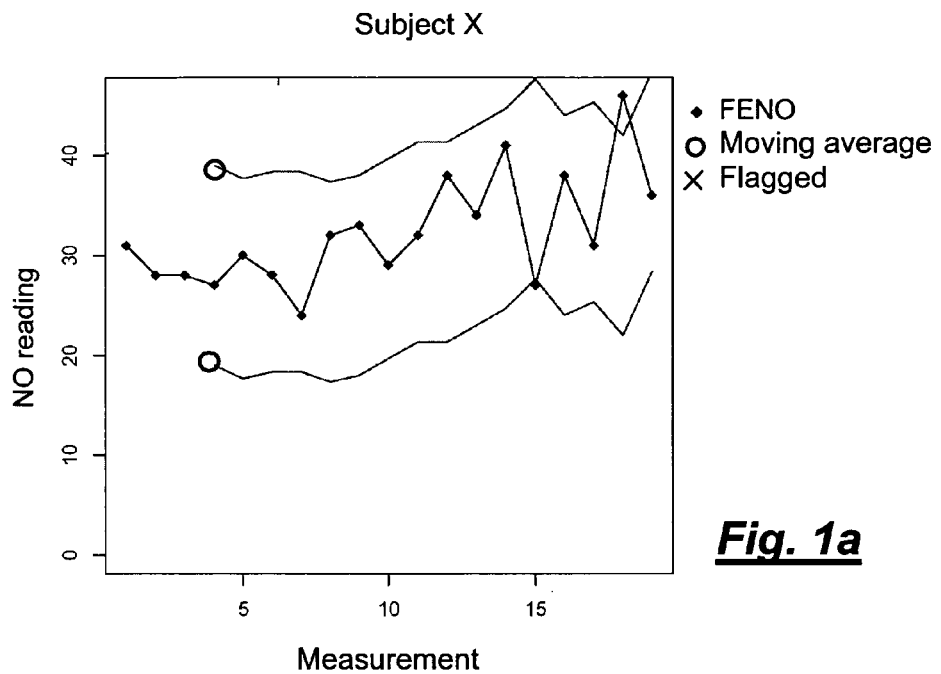
FIGS. 1a and 1b are graphs showing the NO reading (FENO=fractional concentration of nitric oxide in exhaled air) for a reference person (Subject X) at consecutive measurements (FIG. 1a) and the difference between the measures value and the calculated moving average. It can be seen that two measurements exceed the specified deviation of ±10 ppb, most clearly seen in FIG. 1b showing the difference between the current FENO value and the moving average. As the test person was in a normal condition, this outcome indicates that the measurement device is malfunctioning and/or needs to be calibrated.

Before the method described herein is described in detail, it is to be understood that this method is not limited to the particular component parts of the devices described or steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" also include plural referents unless the context clearly dictates otherwise. Thus, for example, reference to "an element" includes more than one such element, and the like.

In this specification and in the claims which follow, reference will be made to a number of terms which shall be defined to have the following meanings:

The term "about" is used to indicate a deviation of +/−2% of the given value, preferably +/−5% and most preferably +/−10% of the numeric values, when applicable.

In the following, the method according to the present invention will partly be described referring to a measuring device measuring the concentration of NO in exhaled breath, measured as ppb (parts per billion). The unit used by the measuring instrument is of course not important, the method can equally be used with measuring instruments using any conventional unit of concentration, e.g. ppm (parts per million). The example of NO, which is measured in ppb, is used to illustrate the accuracy and reliability of the inventive method.

There are many manufacturers of devices for measuring gaseous components in exhaled air, both for research and diagnostic purposes. As explained in the background section, there are different technical approaches to the determination of the concentration of a gas, including different sensors, different chemical analysis etc. The choice of technology is however not material for the present invention, which offers a general method for testing the function of a device for measuring gaseous components in exhaled air. In the following description and enclosed examples, the method will be described in relation to one particular measuring device to facilitate the understanding of the technique described herein. The measuring device in question is the NIOX MINO®, marketed by Aerocrine AB, Solna, Sweden, which is used for diagnostic gas measurements. This device can be used to measure the concentration of nitric oxide in exhaled breath. Such a measurement is often referred to as the measurement of fractional exhaled nitric oxide (FENO), or FENO measurement. The NIOX MINO® adheres to the American Thoracic Society (ATS) 2005 equipment recommendations for measurement of exhaled NO.

In this application an individual who tests or who is used to test the function of a measuring device is called a human control or reference person. According to the technique described herein candidate human controls are qualified according to certain criteria. The qualification of a candidate is called Qualification Procedure. The testing procedure for a device is also carried out using a certain methodology. The inventors have carried out studies for developing the mentioned criteria and methodology. The testing procedure for an instrument is called Biological Test Procedure. In the following an embodiment of the Qualification Procedure for qualifying a candidate Human control for the Biological Test Procedure will be outlined. An embodiment of the Biological Test Procedure will also be described.

EXAMPLES

Summary

The inventors conducted a study to develop and test the criteria and methodology for the Qualification Procedure and the Biological Test Procedure.

In brief, the study confirmed that FENO measurement values from healthy individuals with a limit for the difference between current value and a moving average of ±10 ppb, can be used to test the function of an instrument for FENO measurements.

The inventors also found that measurement values to be excluded, such as values from individuals affected by respiratory tract infection and allergy, can easily be detected in weekly measurements.

The study results surprisingly showed that the rate of false positives, meaning a situation where the malfunction of the device escapes detection, will be below about 0.01%, merely by using two healthy individuals as human controls in weekly procedures.

Equally surprising, statistical analysis of the data indicated that the probability of detecting a faulty instrument with a current FENO value deviation of +15 ppb, was as high as about 92% already when using two healthy individuals as Human controls, in a weekly test procedure.

In summary, the data from the study shows that FENO values derived from healthy individuals can be effectively used as external sources for positive biological testing of the function of a device for FENO measurements.

Background of the Study

The inventors postulated that healthy individuals could be used to test the function of a device for measuring the concentration of a gaseous compound in exhaled breath. The inventors understood that this requires that the healthy individual(s) have reliable and repeatable values with regard to this component, or that a method had to be developed in order to secure the relevance of their values, so that this could serve as an external test of the measuring function of a device.

In the study, focus was placed on diagnostic measurements of NO in exhaled breath, here illustrated by the FENO values from a device for FENO measurements.

Previous studies, e.g. Kharitonov et al., Reproducibility of exhaled nitric oxide measurements in healthy and asthmatic adults and children, Eur Respir J 2003; 21:433-438, Aldeen, Poster ATS 2005—Biological QC via staff self testing at Cleveland Clinic, OH, USA and Marianne Andersson, Poster at ERS, 2005, Long-term variation of exhaled nitric oxide, Staff self testing at Sahlgrenska University Gothenburg, Sweden, have shown that long term intra-individual variation is low.

A long-term study by the inventors, compiling FENO measurements performed for a period of up to 2.5 years by 10 healthy individuals yielded a mean SD (Standard Deviation) of 4.2 ppb, confirming the above results.

Low variability, 8-9%, was also reported by Aldeen, supra, in a study where one healthy individual measured FENO daily for 3.5 months. Kharitonov et al., supra reported a mean pooled SD of 2.11 ppb from standardized FENO measurements performed on five consecutive days in both healthy individuals (n=30, n=number of individuals) and asthmatics (n=29). These data show that a healthy individual is stable in his/her FENO values over long time periods, which indicates that it could be possible to use healthy individuals as Human controls for testing the measuring function of a measuring instrument.

One aim of this study was to investigate the feasibility of using healthy individuals as an external source of reference to confirm the accurate function of devices for measuring the concentration of a gaseous compound in exhaled breath, and in particular for a device for FENO measurements. Another aim was to determine statistically and clinically appropriate limits for the allowed individual variations.

Performing the Study

The study was divided into two parts. The purpose of part 1 was to establish reference limits for individual FENO values. Such limits would be used in qualifying individuals to be used as human controls. The hypothesis of the inventors was that it could be possible to use individuals as a source for a positive biological test in order to test if a device for measuring the concentration of a gaseous compound in exhaled breath is functioning properly. The results from part 1 of the study are disclosed in the following.

During part 1, FENO values were obtained during a three week measurement period where 17 individuals took part. Values from 15 of these individuals were used to calculate individual standard deviation (SD) and upper and lower reference limits (see Table 1) in order to evaluate if the individuals would qualify as Human controls.

TABLE 1

Mean ppb for all days and reference limits
Mean ppb, standard deviation (SD), number of measurement days of individual FENO, the normal distribution z-coefficients at 95% and 99% confidence intervals, lower (LL) and upper (UL) confidence intervals, for each individual over all study days in part 1 (n = 15).

| Subject# | Mean | days | SD | 95% Z (0.05) | LL | UL | 99% Z (0.01) | LL | UL |
|---|---|---|---|---|---|---|---|---|---|
| 1 | 9.2 | 14 | 1.47 | 1.96 | 6.4 | 12.1 | 2.58 | 5.5 | 13.0 |
| 2 | 8.7 | 13 | 1.51 | 1.96 | 5.8 | 11.7 | 2.58 | 4.9 | 12.6 |
| 4 | 8.3 | 14 | 1.71 | 1.96 | 5.0 | 11.7 | 2.58 | 3.9 | 12.7 |
| 5 | 25.0 | 14 | 2.66 | 1.96 | 19.8 | 30.2 | 2.58 | 18.1 | 31.8 |
| 6 | 13.8 | 13 | 1.23 | 1.96 | 11.4 | 16.2 | 2.58 | 10.7 | 17.0 |
| 7 | 29.3 | 11 | 4.13 | 1.96 | 21.2 | 37.4 | 2.58 | 18.6 | 39.9 |
| 8 | 15.4 | 4 | 1.05 | 1.96 | 13.3 | 17.4 | 2.58 | 12.7 | 18.1 |
| 9 | 12.3 | 15 | 1.78 | 1.96 | 8.8 | 15.8 | 2.58 | 7.7 | 16.9 |
| 10 | 17.4 | 14 | 1.98 | 1.96 | 13.6 | 21.3 | 2.58 | 12.3 | 22.6 |
| 11 | 7.2 | 5 | 0.89 | 1.96 | 5.5 | 9.0 | 2.58 | 4.9 | 9.5 |
| 12 | 9.7 | 15 | 1.22 | 1.96 | 7.3 | 12.1 | 2.58 | 6.5 | 12.8 |
| 13 | 17.9 | 13 | 1.66 | 1.96 | 14.7 | 21.2 | 2.58 | 13.6 | 22.2 |
| 14 | 13.8 | 13 | 3.76 | 1.96 | 6.4 | 21.2 | 2.58 | 4.1 | 23.5 |
| 16 | 17.5 | 7 | 0.71 | 1.96 | 16.1 | 18.9 | 2.58 | 15.7 | 19.3 |
| 17 | 19.0 | 12 | 2.48 | 1.96 | 14.2 | 23.9 | 2.58 | 12.6 | 25.4 |
| Mean | 15.0 | 11.8 | 1.9 | | | | | | |
| Min | 7.2 | 4.0 | 0.7 | | | | | | |
| Max | 29.3 | 15.0 | 4.1 | | | | | | |
| SD | 6.3 | | | | | | | | |

In part 2 of the study, one aim was to collect long-term data to check if healthy individuals could be used to test the measuring function of a device for measuring the concentration of a gaseous compound in exhaled breath, exemplified by a device for FENO measurements.

The healthy control individuals participating in part 1 of the study continued to perform weekly measurements during part 2 of the study. The individual reference limit was based on the moving average calculation principle using the three previous weekly values and the measurement result of the current day. In the alternative, the qualification period can be shortened, e.g. to only one or 1.5 weeks by iterating the qualification procedure, and measuring the concentration of the exhaled gas every day, every second day, or every third day.

Each value was determined to be normal or abnormal using the definitions below.

A normal measurement is defined as a measurement that does not differ from the mean of the three previous normal measurements by more than ±10 ppb. The measurement should advantageously not be taken when the human control is ill or affected by other factors that can influence NO levels.

Consequently, an abnormal measurement is defined as a measurement that differs from the mean of the three previous normal measurements by more than ±10 ppb.

A first hypothesis of the inventors was to define the reference limit for an individual as the estimated mean individual FENO value ±2SD. The estimated mean individual FENO value is thereby derived from a qualification period of 10 measurements performed during a 3-week period. However, the inventors concluded that this definition had the disadvantage of not taking into consideration slow but physiological changes over time, the baseline for an individual could remain the same for a long time, e.g. for many years. This means that an individual that for some reason has a period with somewhat higher or lower values (where the values still may have a low variability) compared to the qualification period, might falsely cause a device to be indicated to give an incorrect reading (a false negative). To circumvent this disadvantage, the inventors developed another method that would allow for drifts over time, without implying instrument defects. The method chosen for evaluation was the determination of a moving average for each human control.

For the purpose of the method according to one embodiment of the invention, i.e. the embodiment focused on devices for the measurement of NO, a person qualifies as a human control if the mean of a series of 6-10 measurements over a 2 week period is between 10 and 40 ppb. As stated above, the qualification period can be shortened, e.g. to only one or 1.5 weeks by iterating the qualification procedure. An example is given below:

An individual will measure FENO values n (n is a number) days in a row which gives n test values.

After n days the mean is calculated as $$\frac{t_1 + \ldots t_n}{n} = \text{Mean } X_n \ (n = 6\text{-}10)$$

The mean $X_n$ should be between 10-40 ppb in order for the individual to qualify as a human control.

After day n in the measurement period above, the human control will continue with weekly measurements. The individual reference limit will be based on a moving average. The moving average will be based on at least the two, preferably at least the three latest measured weekly values. According to a specific embodiment, also the measurement of the current day is included in the calculation of the moving average. Alternatively, the qualification process is shortened, as explained earlier in this description.

To illustrate this, another example is given: A human control A will measure his/her FENO values four weeks in a row which gives four test values:

$R_{A:t}$, $R_{A:t-1}$, $R_{A:t-2}$ and $R_{A:t-3}$ where $R_{A:t}$ is the current FENO reading for tester A, $R_{A:t-1}$ is the most recent previous valid reading, $R_{A:t-2}$ is the 2nd most previous valid reading, and $R_{A:t-3}$ is the 3rd most recent previous valid reading.

The moving average is calculated as follows:

$$\frac{R_{A:t-1} + R_{A:t-2} + R_{A:t-3}}{3}$$

When including the current value, the moving average is calculated for example as:

$$(R_{A:t} + R_{A:t-1} + R_{A:t-2} + R_{A:t-3})/4$$

The difference between the current value and the moving average is calculated as follows:

$$d_A = R_{A:t} - \frac{R_{A:t-1} + R_{A:t-2} + R_{A:t-3}}{3}$$

Also here, the current value can be included in the calculation of the moving average. If $d_A$ is not within ±10 ppb, then the measurement is defined to be out of range.

In part 2 of the study, another aim was to collect long-term data to investigate the validity of the suggested procedure for testing the function of a measuring device by using human controls. In this part of the study, the individuals that took part in part 1 of the study continued to perform weekly measurements. The individual reference limit was based on the moving average calculation principle using the three previous weekly values and the measurement result of the current day. Each value was marked as normal or abnormal using the definitions stated above.

This implies that the difference between a current individual FENO value and the moving average from the previous three tests needs to be within ±10 ppb in order for the value to be accepted.

Thus, in the second part of the study it was investigated whether FENO values measured once a week, during an extended period of time, were within the expected reference limits, calculated by using a moving average for the measurement values of the Human control and as defined above.

Part 2 of the study was performed during 3 months and the results presented here cover the weekly FENO measurements performed by 15 individuals using devices for measuring FENO values.

For the purpose of this study, it was decided that a candidate human control is qualified to become a human control if a series of 6-10 measurements taken over a 2-week period has a mean value in the range 10 ppb to 40 ppb (excluding measurements when the candidate human control is known to be ill).

It was also decided to use the technique of difference between a moving average and the current measurement value to determine if measurement values were out of range or not. The reason for this approach has been explained above and will be further commented later.

It was further decided that a difference of 7 ppb or more between two measurements in the instrument triggers a repetition of two measurements in the same instrument.

Test Design

In part 2 of the study, the measurements were performed by healthy individuals, once a week, at daytime between 8 AM and 6 PM. Each individual performed two successful measurements consecutively.

FENO was measured at an exhalation flow rate of 50 ml/s according to ATS (American Thoracic Society) guidelines. The device was calibrated at sensor manufacturing with calibration gas 200 ppb NO nominal.

Subjects

The study subjects (n=15) were between 33-59 years of age. All subjects taking part in the study were trained in the handling of the instruments. Further, in order to be included in the study the individuals had to fulfil the following inclusion criteria:

a healthy adult, age 18-65 years
no known viral infection/airway disease at the time of inclusion
no asthma diagnosed (or well-controlled, medicated asthma)
no history of smoking within one year before the study
stable FENO levels 10-40 ppb based upon previous experience The test subjects were instructed to note the following in a case report form at each occasion:

symptoms of respiratory infection
ongoing allergy (including name of any medication taken)
prescribed medication taken in the morning and/or evening (name of the medication and reason for intake to be documented)
intake of nitrate-rich food within 3 hours before the occasion of measurement
strenuous physical exercise within 1 hour before measurement
side effects Statistical Methods Definition of a successful measurement: A difference between the first and second measurement of 7 ppb or more is considered to be out-of-range, i.e. not approved.

All statistical tests were parametric. A measurement value or other value with a p-value <0.05 was considered statistically significant. A p-value of 0.05 means that the probability that the related value is correct is 95% (1−0.05=0.95). When measurement results were recorded as <5 ppb, the value has been set to 4 ppb. The choice of the limit <5 ppb is because the lower measurement limit for the device used in the study (NIOX MINO®) is 5 ppb. The reason for setting the value to 4 ppb is that it is necessary for the calculation of the moving average to assign a value also to readings below the measuring limit of 5 ppb.

Definition of Moving Average: The individual reference limit was be based on a moving average calculation. The moving average was be calculated from the average of the previous three valid measurements subtracted from the current reading. The principle of a moving average calculation has been explained above.

Differences in measurement values between the instruments were tested with the standard two-sided t-test.

Results

General

A total of 152 measurements (in duplicate) from 15 individuals were analysed after 3 months. The individuals performed required measurements on all weeks, except on vacation weeks. On 3 occasions, the FENO values differed with 7 ppb or more. Measurements repeated by two individuals in NIOX MINO, showed acceptable difference between replicates.

Three individuals reported intake of chronic medication. One individual took medication for hay fever, one for allergy and one for arthritis. Three individuals reported seasonal allergy. One individual reported allergy symptoms. Five individuals reported symptoms of respiratory tract infection during some measurement days of the study period. One individual suffered from an acute ear inflammation during the later half of the measurement period.

Two individuals reported consumption of nitrate-rich food on two single occasions before measurements. One individual started a Very Low Calorie Diet (VLCD) during the first week of measurements, which ended after 9 weeks. One individual had a known food allergy.

No individual reported exercise before measurements.

Missing Values

Most individuals performed at least 10 measurements during the reported three month test period. Vacation was the only reason for not performing the weekly measurement.

FENO Measurement Results

Mean FENO values from part 2 of the study were between <5 and 43.5 ppb. The results from all individual measurements are presented below in Table 2, where mean, min, max and SD (standard deviation) are presented. The maximum individual SD was 7.98 ppb.

TABLE 2

Overall individual results
Number of tests (n), mean, standard deviation (SD), min and max FENO values.

| Individual Number | n | Mean | SD | Minimum | Maximum |
|---|---|---|---|---|---|
| 1 | 10 | 11.7 | 2.87 | 6.5 | 15.5 |
| 2 | 11 | 13.2 | 3.83 | 8.5 | 20.5 |
| 4 | 10 | 9.3 | 1.75 | 6.5 | 12.0 |
| 5 | 10 | 27.0 | 3.77 | 20.0 | 33.0 |
| 6 | 11 | 18.1 | 3.68 | 13.0 | 27.0 |
| 7 | 9 | 33.8 | 4.12 | 28.0 | 39.5 |
| 8 | 10 | 16.7 | 2.64 | 11.5 | 21.0 |
| 9 | 10 | 15.3 | 7.02 | 7.0 | 32.5 |
| 10 | 10 | 16.1 | 2.65 | 13.0 | 20.0 |
| 11 | 13 | 16.5 | 5.73 | 11.0 | 32.5 |
| 12 | 10 | 11.6 | 6.17 | <5.0 | 27.0 |
| 13 | 9 | 28.6 | 7.98 | 20.5 | 43.5 |
| 14 | 9 | 14.2 | 4.00 | 10.5 | 24.0 |
| 16 | 10 | 17.0 | 4.42 | 11.5 | 27.0 |
| 17 | 10 | 20.8 | 2.82 | 15.0 | 23.0 |

Graphical Presentation of FENO Values and Moving Average

Figure 1B:
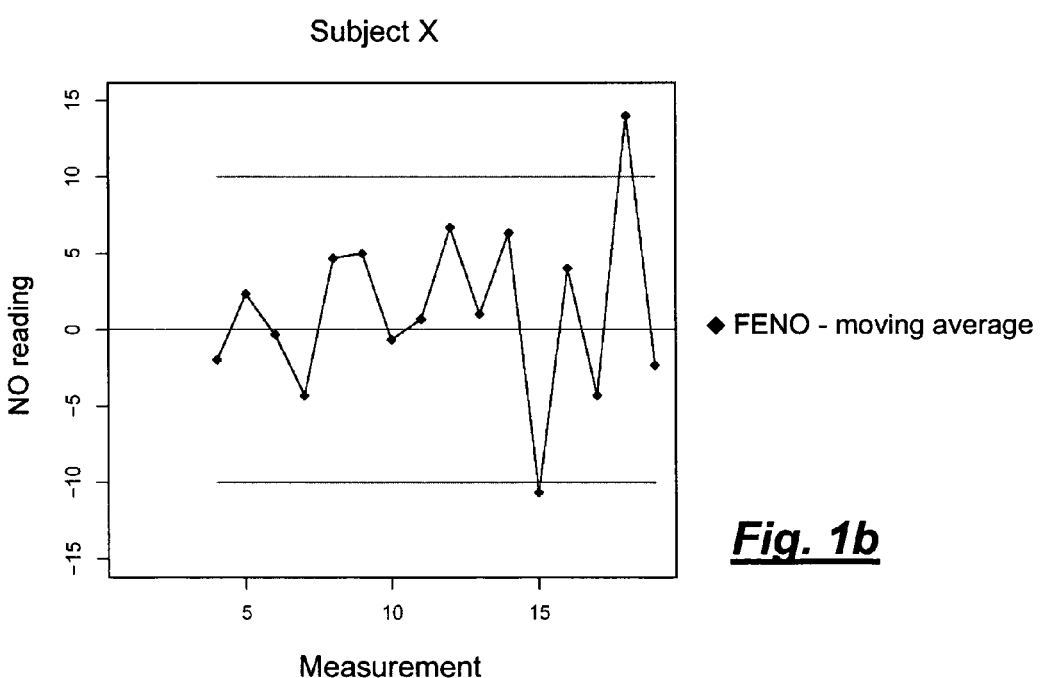
Figure 2A:
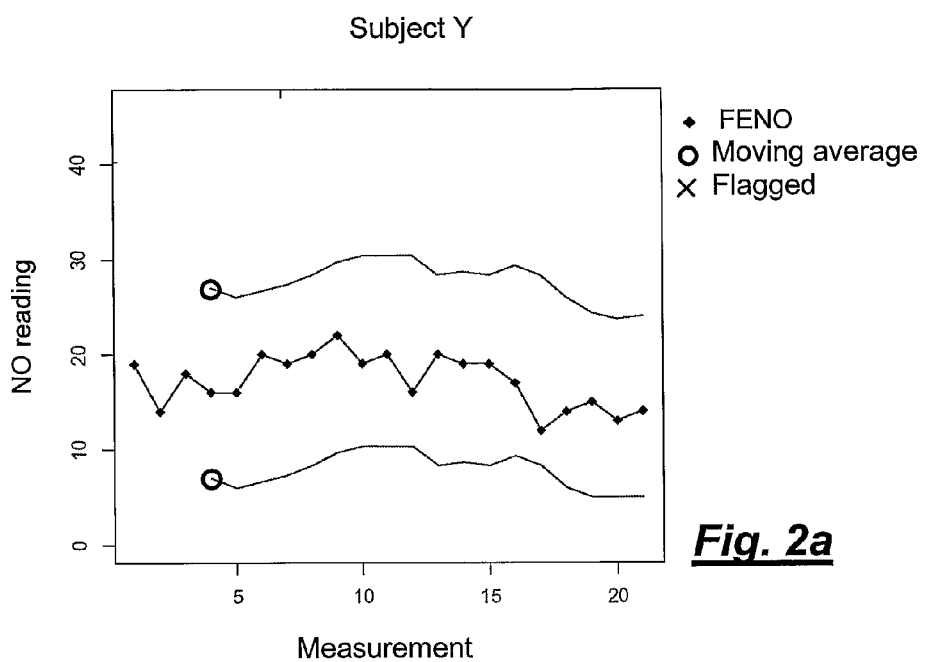
FIGS. 2a and 2b are graphs like the above, however showing a case where the reference person (Subject Y) exhibits only small variations, and where the device functions well during the entire measurement period.
Figure 2B:
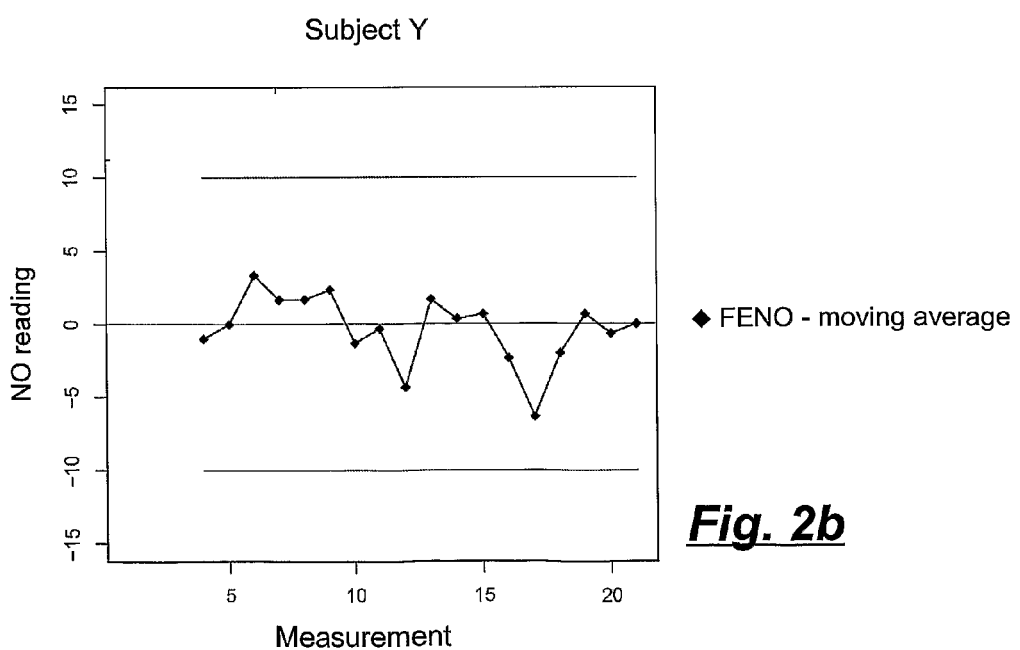
Figure 3A:
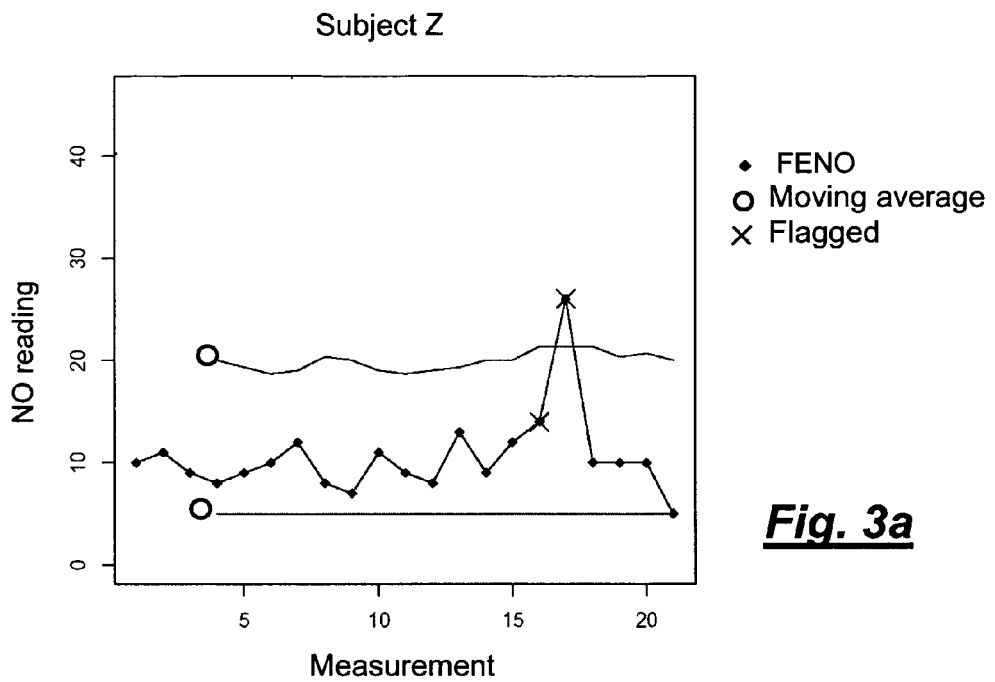
FIGS. 3a and 3b show a case where the reference person (Subject Z) has indicted (flagged) that he/she suffers from some temporary airway problems, such as allergy or a cold. These values can therefore be disregarded.
Figure 3B:
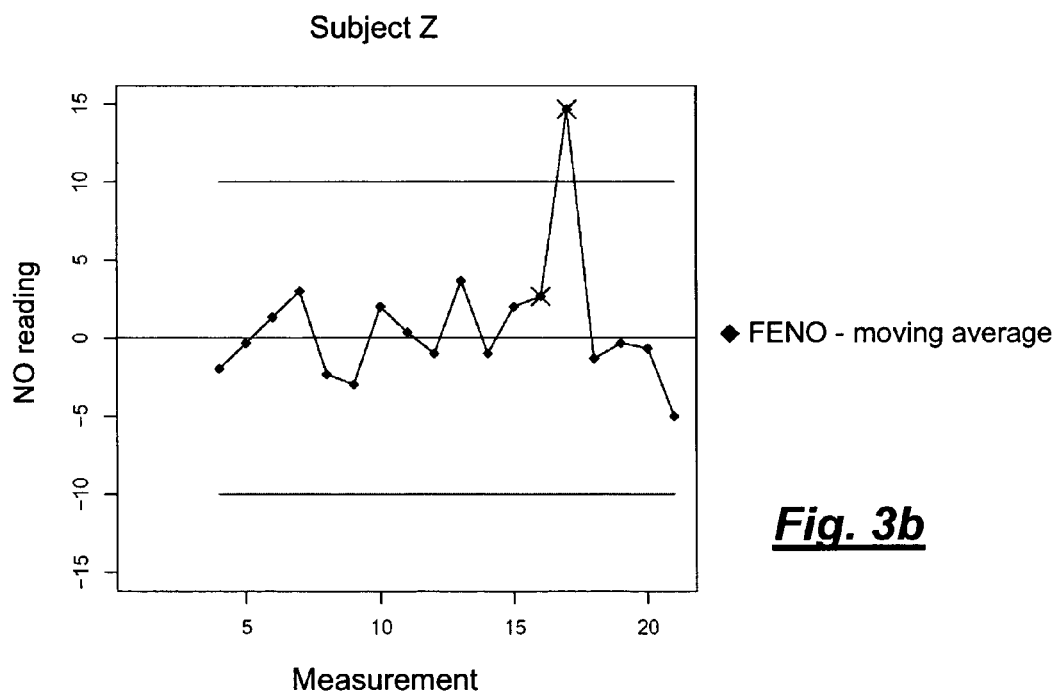
Figure 4:
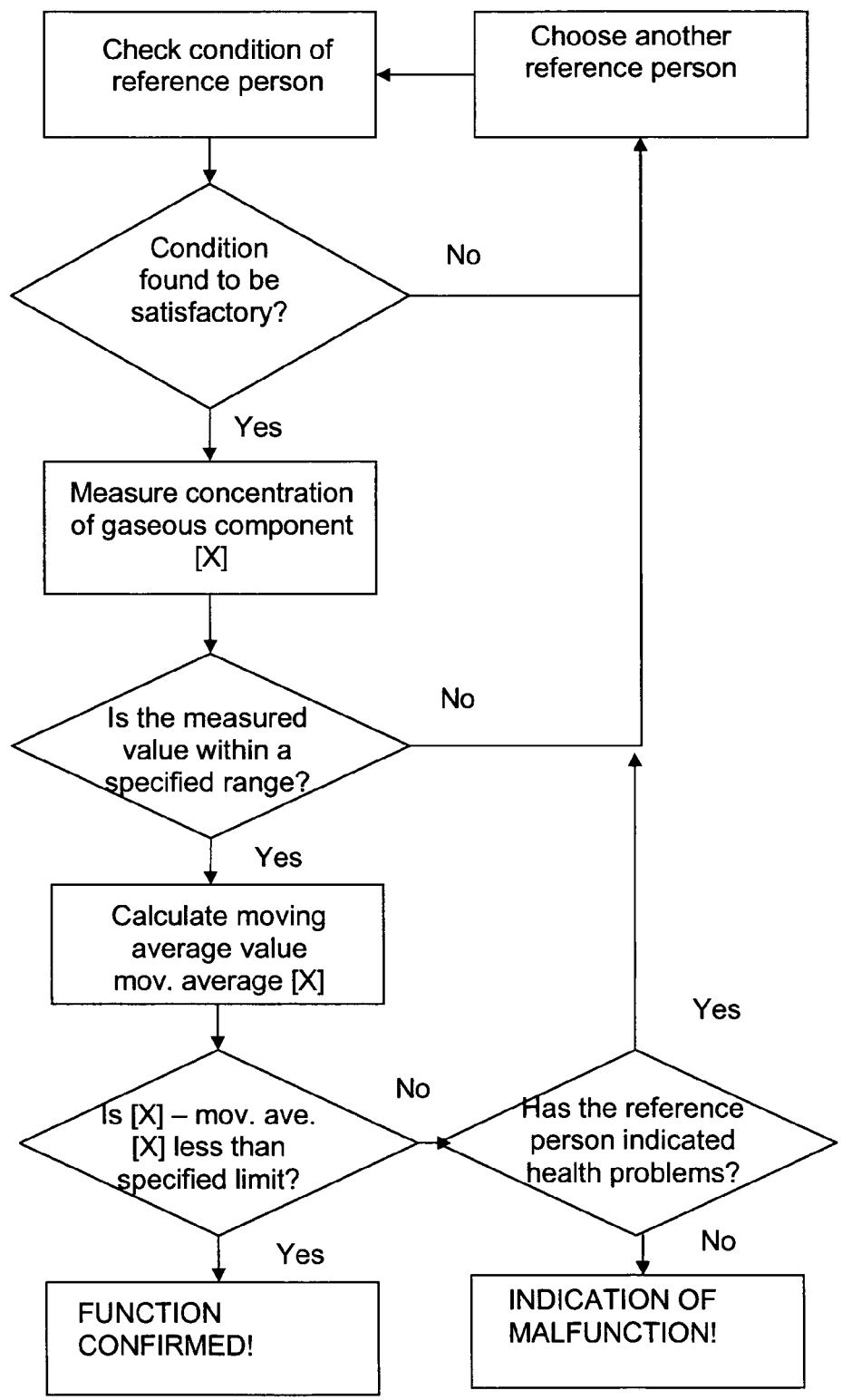
FIG. 4 is a block diagram showing the basic steps of an embodiment of the invention, a structured procedure ending in the confirmation of the correct function of the device, or the indication of malfunction of the device.

In FIGS. 1a, 1b, 2a, 2b, 3a, and 3b, the FENO values and moving averages are presented. The top graphs (FIGS. 1a, 2a, and 3a) show a graphical presentation of the individual FENO values for each test individual (black diamonds), together with the maximum (upper line marked with a circle) and minimum (lower line marked with a circle) allowed limits from the calculated moving average.

The lower graphs (FIGS. 1b, 2b, and 3b) show the difference between the current FENO value and the moving average together with the maximum and minimum allowed limits. For both cases, if the difference was outside ±10 ppb, the value was defined as out of range. The flagged values in the graphs were values that the individual had commented upon. The comments were related to symptoms of cold, allergy, intake of nitrate rich food and intake of inflammatory medication.

Six individuals showed a difference between the moving average and the current FENO value that was outside the ±10 ppb limit. Four of these individuals reported respiratory tract infection at the time of the measured values. One individual reported intake of several medications against allergy during the whole test period. Another individual reported chronic medication with celecoxib (Celebra®), an anti-inflammatory drug, during the whole study period.

As can be seen in the graphs, the method is accurate in detecting fluctuations in FENO values that are due to factors that are known to influence the FENO value, such as respiratory tract infection and nitrate-rich food intake.

Evaluation of Sensitivity of Using Moving Average in a Biological Test Procedure In order to test the sensitivity of using moving average in the Biological Test Procedure, the inventors used bootstrap estimates and calculated the probability of failing the Biological Test Procedure.

Bootstrap estimates were based on the current data derived in part 1 and 2 of this study. For a detailed explanation of the bootstrap method, see Bradley Efron and R. J. Tibshirani, An introduction to the Bootstrap (Monographs on statistics and Applied Probability), 1995. There were in total 253 normal measurements with at least 3 preceding normal measurements from which the moving average could be calculated. These measurements were distributed over 15 individuals. The average time span of the measurements is 118 days. Each estimate is from 10,000 bootstraps.

Two estimates are given, each for a range of possible device states. The inventors have for all calculations assumed that two Human controls are available in each case.

First, the inventors estimated the probability of failing the Biological Test Procedure in case of performing a single Biological Test Procedure; when a fault in a measuring instrument is present. This is an estimate of the probability that the fault will be detected by the Biological Test Procedure.

Second, the probability of failing at least one Biological Test Procedure in two consecutive Biological Test Procedures was estimated; when a fault in a measuring instrument is present. This is an estimate of the probability that the fault will be detected in two consecutive Biological Test Procedures.

For each bootstrap, two individuals were randomly selected, weighted by the number of normal measurements available for each individual. For each individual, normal measurements from two consecutive dates with at least 3 preceding normal measurements were randomly selected. The Biological Test Procedure was performed on these selections. The estimates are the proportion of times that the bootstrap selection failed the Biological Test procedure.

In order to simulate out-of-calibration, the measurement for a particular date had an error added to it (+5 ppb, +10 ppb, +15 ppb, −10 ppb, −15 ppb). This measurement error was then compared to the (unchanged) average of the previous three normal measurements. If the measurement was deemed normal, in the case of the two consecutive Biological Test Procedures, the average was updated to reflect this.

The results show that the false positive rate is about 0.02% after two consecutive Biological Test Procedures (i.e. on two separate occasions), and that the probability of detecting an increase of +15 ppb in the Human control as an out of range measurement is about 92% after one Biological Test Procedure, and about 95% after two consecutive Biological Test Procedures.

For example, the false positive rate (the probability that a normally functioning measuring instrument, e.g. the NIOX MINO, fails the Biological Test Procedure) is about 0.02% after two Biological Test Procedures. Further, the probability of detecting a +15 ppb bias (i.e. that the reading of the measuring instrument is 15 ppb too high) with two Human controls is about 92% after one Biological Test Procedure, and about 95% after two consecutive Biological Test Procedures.

The study showed that by using two human controls and the outlined moving average technique, both the goals of high sensitivity and low false positive rate were achieved.

The outlined moving average technique has the advantage of allowing for some biological FENO fluctuations over time compared to having a fixed baseline. If changes over time were not taken into consideration, individuals having a period with somewhat higher or lower FENO values compared to the mean value acquired during the qualification period would lead to a false positive.

The reason for choosing ±10 ppb for the limit for the difference between a measured value and the value of the moving average, in this particular embodiment, is that there are a number of inaccuracy factors to consider. First, the biological inaccuracy for FENO is ±2.5 ppb within one SD. To include the majority of individuals, 3 SD should be applied, which is equivalent with ±7.5 ppb. Since a reasonable inaccuracy is ±2.5 ppb for the measuring device, the accumulated inaccuracy will be ±10 ppb.

The FENO values obtained during part 2 of the study show that the sensitivity for the methodology to detect changes in FENO values is very good. In four individuals, values out of range were detected during respiratory tract infections. In two further individuals, periods with allergic symptoms produced out of range values. Apart from these occasions there were very few instances with false positives out of range values, which shows that the outlined moving average technique is a feasible way of performing a test of the measuring function of an instrument for measuring FENO, by using healthy individuals as reference.

Hence, as shown using FENO values from healthy individuals with a limit for the difference, between current value and a moving average, of ±10 ppb, the method according to the invention is a feasible approach to simply and inexpensively test the function of a device measuring the concentration of a gaseous compound in exhaled breath.

In particular, the performed study and analysis shows that FENO measurement values derived from healthy individuals can be effectively used for positive biological testing of the function of a device for the determination of exhaled NO.

Based on the study and analysis described above, the inventors have outlined a Qualifying Procedure and a Biological Test Procedure as described in the following.

Qualifying Procedure

In the qualifying procedure, normal values were established for the individual(s) who are scheduled to perform the Biological Test Procedure. A minimum of one individual, but preferably two or more individuals, need to undergo the Qualifying Procedure. It may be advantageous that also a third individual undergoes the Qualifying Procedure, as this third individual may then function as a back-up, e.g. in the case that one or more of the regular individuals is prevented from taking part in the Biological Test Procedure.

A candidate human control will be qualified during a two week period. When the candidate Human control performs the measurements, the measuring instrument is used as in normal use. Measurement values are entered into a Personal Qualification Tester Log of the candidate Human control.

In order to stay qualified, a human control should advantageously perform weekly measurements and enter the measurement values into his or her Personal Qualification Tester Log and his or her Weekly human control Log. It is suggested that the qualification is suspended if the most recent Normal Measurement is older than a month, and resumed when the human control is able to perform three Normal Measurements over the course of a week.

The Qualification Procedure preferably starts by the identification of one, preferably two or more, candidate human controls that will be used for the Biological Test Procedure and who fulfil the following criteria:
1. at least 18 years of age
2. no ongoing cold or known airway disease
3. not diagnosed with asthma, or having a well-controlled, medicated asthma
4. is a non smoker
5. has expected FENO values between 10 and 40 ppb
6. preferably has no allergy (except seasonal, see below)

The following should advantageously also be considered in order to obtain reliable results:

Before any measurement a human control or candidate human control should
7. avoid nitrate rich food within 3 hrs before the measurement, and
8. avoid any strenuous exercise at least 1 hour before the measurement.

Further, no measurements should be performed in case of
9. an ongoing cold, or
10. acute seasonal allergy.

Advantageously 6-10 FENO measurements once a day should be performed during a two week period, and the recorded values entered in the Personal Qualification Tester Log.

The mean values are then calculated. This value should fall within the interval of about 10 to about 40 ppb.

In this application the term "normal condition" is used to indicate the condition of an individual. Basically, an individual who fulfils the above criteria 1 through 6 is considered to be in a normal condition. However, an individual should also fulfil the criteria 7 and 8, and preferably no measurement should be taken when the events according to criteria 9 and 10 occur.

Biological Test Procedure

The Biological Test Procedure described below is an embodiment of the method according to the invention. It should advantageously only be performed by individuals that have been qualified as human controls for the Biological Test Procedure. Advantageously, two human controls should be available. If the measurement by the first human control is not approved, then the second human control should take or make a measurement. If also the measurement by the second human control is not approved, then the measuring instrument should be removed from service. Advantageously, the technical support of the manufacturer of the measuring instrument should then be contacted.

If only one human control is available, and the measurement is not approved, the measuring instrument should be temporarily removed from service until a second qualified human control is available and the Biological Test Procedure is then repeated.

The following is an example of a procedure for performing a test within the Biological Test Procedure:
1. Check that the measuring instrument is equipped for measuring, e.g. that the correct sensor is mounted. It is conceivable that the measuring instrument indicates that the Biological Test Procedure has been entered, e.g. with a symbol on the display of the device.
2. Ensure that the measuring instrument is ready for measuring. Then perform a measurement, advantageously according to the procedure described in the user manual.
3. Wait for the result of the measurement (test result) to be displayed.
4. Enter the test result into a "weekly human control Log" and into a "measuring instrument Tester Log".
5. Calculate the mean value for the human control's previous three test results in the "weekly human control Log". Subtract the value of the current test result from the calculated mean value to get the difference. See the "Weekly human control Log" for details on the calculation. According to a particular embodiment, the current test result is approved if the difference is within ±10 ppb. In alternative embodiments, e.g. adapted for other measuring devices different limits for an approved test result are conceivable.
6. In case the measurement is NOT approved, the instrument should be taken out of service until a second human control is available. However, if a second human control is available, it is advantageous to perform the entire Biological Test Procedure from the beginning (step 1 and onwards) with a second human control. The Biological Test Procedure is approved if the second human control's measurement is approved according to the criteria described under point 5.

The measuring instrument should be taken out of service if also the test result of the second human control is not approved.

If repeated measurements for two days in a row show values lower than the lower measuring limit of the instrument (for the NIOX MINO this limit is 5 ppb), or if the Biological Test Procedure is not approved, one should not use the measuring instrument. Advantageously the manufacturer should be contacted in such a case.

If a test within the Biological Test Procedure (point 1-5 above) is not approved, it should preferably be checked if the human control has unknowingly developed any kind of allergy, as an allergy may cause higher than normal values. Likewise, it should be ruled out that the human control has contracted a cold, eaten any nitrate-rich food, taken any anti-inflammatory drug, or exercised within the previous hour.

Measurements may be performed at any time of the day. However, it is recommended to perform the measurements at the same time of the day every day.

The inventive method and its embodiments have been described in relation to a device for FENO measurements, and more specifically using the NIOX MINO® (Aerocrine AB, Solna, Sweden) as an example of a measuring device. Naturally, the technique described herein can be used also with other devices for measuring a gaseous component in exhaled breath. Similarly, technique described herein may also be used in case of measuring instruments for measuring other substances in exhaled breath than nitric oxide.

Necessary adjustments can easily be performed by a person skilled in the relevant art, depending on the accuracy of the device, the diagnostic interval of the gaseous component etc. For example, the ±10 ppb limit for the difference between current value and the moving average value may be necessary to adjust depending on the specifications and performance of different devices.

Although particular embodiments have been disclosed herein in detail, this has been done by way of example for purposes of illustration only, and is not intended to be limiting with respect to the scope of the appended claims that follow. In particular, it is contemplated by the inventor that various substitutions, alterations, and modifications may be made to the invention without departing from the spirit and scope of the invention as defined by the claims.

The invention claimed is:

1. A method of using a human control for testing the function of a device for measuring the concentration of a gaseous substance in exhaled air, the method comprising the steps of:
    checking that said human control is in a normal condition,
    measuring the concentration of said gaseous substance in air exhaled by said human control to obtain a current value,
    determining if said current value of the measured concentration is within a specified range,
    determining a reference value by calculating a moving average based on the current value and previously obtained values from measurements with the same human control,
    determining the difference between said reference value and said current value, and
    interpreting a deviation of more than a specified value as an indication that the device is malfunctioning.

2. The method according to claim 1, wherein said specified range is adapted to the relevant diagnostic interval for the gaseous component to be determined.

3. The method according to claim 1, wherein at least two measurement values from previous measurements are used when determining the moving average.

4. The method according to claim 1, wherein at least three measurement values are used when determining the moving average.

5. The method according to claim 1, wherein measurements are performed at an interval of at least 2 days but less than 8 days.

6. The method according to claim 1, wherein said gaseous substance is chosen among carbon dioxide, oxygen, nitric oxide, and volatile organic compounds detectable in exhaled air.

7. The method according to claim 1, wherein said gaseous substance is nitric oxide.

8. The method according to claim 1, wherein the specified range for the current value is about 10 to about 40 ppb nitric oxide.

9. A method of using a human control for testing the function of a device for measuring the concentration of a gaseous substance in exhaled air, the method comprising the steps of:
    checking that said human control is in a normal condition, wherein a human subject is considered to qualify as a control and as being in a normal condition when fulfilling the following criteria: no ongoing cold, no airway disease, no asthma, non-smoker, no allergy, no non-seasonal allergy, no intake of nitrate rich food within the last 3 hours, and no strenuous exercise performed within the last hour,
    measuring the concentration of said gaseous substance in air exhaled by said human control to obtain a current value,
    determining if said current value of the measured concentration is within a specified range,
    determining a reference value,
    determining the difference between said reference value and said current value, and
    interpreting a deviation of more than a specified value as an indication that the device is malfunctioning.

10. The method according to claim 9, wherein the interpretation of a deviation of more than a specified value as an indication that the device is malfunctioning is preceded by, and conditional to, an additional check that the control is in a normal condition.

11. The method according to claim 9, wherein said specified range is adapted to the relevant diagnostic interval for the gaseous component to be determined.

12. The method according to claim 9, wherein the reference value is determined by calculating a moving average based on the current value and previously obtained values from measurements with the same human control.

13. The method according to claim 12, wherein at least two measurement values from previous measurements are used when determining the moving average.

14. The method according to claim 12, wherein at least three measurement values are used when determining the moving average.

15. The method according to claim 12, wherein measurements are performed at an interval of at least 2 days but less than 8 days.

16. The method according to claim 9, wherein said gaseous substance is chosen among carbon dioxide, oxygen, nitric oxide, and volatile organic compounds detectable in exhaled air.

17. The method according to claim 9, wherein said gaseous substance is nitric oxide.

18. The method according to claim 9, wherein the specified range for the current value is about 10 to about 40 ppb nitric oxide.

* * * * *